United States Patent
Kusner et al.

(10) Patent No.: US 8,771,182 B2
(45) Date of Patent: Jul. 8, 2014

(54) METHOD FOR ELECTRONIC ADJUSTMENT OF ILLUMINANCE OF SURGICAL LAMP

(75) Inventors: Mark Kusner, Gates Mills, OH (US); Michael A. Centanni, Parma, OH (US)

(73) Assignee: STERIS Corporation, Mentor, OH (US)

( * ) Notice: Subject to any disclaimer, the term of this patent is extended or adjusted under 35 U.S.C. 154(b) by 228 days.

(21) Appl. No.: 13/441,033

(22) Filed: Apr. 6, 2012

(65) Prior Publication Data

US 2012/0253138 A1 Oct. 4, 2012

Related U.S. Application Data

(62) Division of application No. 12/267,798, filed on Nov. 10, 2008, now Pat. No. 8,172,751.

(51) Int. Cl.
*A61B 1/06* (2006.01)

(52) U.S. Cl.
USPC .......................................... 600/249; 362/804

(58) Field of Classification Search
USPC ................... 600/248, 249, 178–182, 199; 362/572–575, 804
See application file for complete search history.

(56) References Cited

U.S. PATENT DOCUMENTS

| | | | |
|---|---|---|---|
| 3,774,988 A * | 11/1973 | Rogers | 359/275 |
| 4,517,632 A * | 5/1985 | Roos | 362/389 |
| 4,585,312 A | 4/1986 | Ishiwata et al. | 359/268 |
| 4,872,745 A | 10/1989 | Fujisawa et al. | 359/268 |
| 4,884,008 A * | 11/1989 | Bossler et al. | 315/152 |
| 4,920,257 A | 4/1990 | Fuerthbauer et al. | 250/201.1 |
| 5,001,616 A * | 3/1991 | Gehly et al. | 362/308 |
| 5,375,049 A | 12/1994 | Witt | 362/418 |
| 5,383,105 A | 1/1995 | Agut | 362/285 |
| 5,497,295 A | 3/1996 | Gehly | 362/32 |
| 5,803,905 A * | 9/1998 | Allred et al. | 600/249 |
| 6,081,371 A | 6/2000 | Shioda et al. | 359/372 |
| 6,160,582 A | 12/2000 | Hill | 348/370 |
| 6,791,738 B2 | 9/2004 | Reynolds et al. | 359/265 |
| 6,963,437 B2 | 11/2005 | Bauer et al. | 359/24 |
| 8,050,547 B2 | 11/2011 | Fornasiero | 396/4 |
| 2002/0089857 A1 | 7/2002 | Borders et al. | 362/399 |
| 2002/0113941 A1 | 8/2002 | Bees | 351/200 |
| 2007/0047074 A1 | 3/2007 | Feinbloom et al. | 359/380 |
| 2007/0100326 A1 | 5/2007 | Smith | 606/4 |
| 2009/0318772 A1 * | 12/2009 | Marka et al. | 600/249 |

\* cited by examiner

*Primary Examiner* — Mary Hoffman
*Assistant Examiner* — Tara Carter
(74) *Attorney, Agent, or Firm* — Kusner & Jaffe; Michael A. Centanni

(57) ABSTRACT

The present invention provides a method of controlling a light output of a surgical lamp used for illuminating a surgical site. The surgical lamp includes a housing that defines an internal cavity. A light source is disposed within the internal cavity of the housing. The light source produces a light path and a light field at a surgical site that is remote from the housing. The method comprises providing a voltage sensitive device along the light path, the voltage sensitive device having light transmissive properties that change in response to a biasing voltage applied thereto, and applying a biasing voltage to the voltage sensitive device to achieve a desired light intensity at the surgical site.

6 Claims, 6 Drawing Sheets

METHOD FOR ELECTRONIC ADJUSTMENT OF ILLUMINANCE OF SURGICAL LAMP

RELATED APPLICATION

This application is a divisional of application Ser. No. 12/267,798 filed on Nov. 10, 2008 now U.S. Pat. No. 8,172,751.

FIELD OF THE INVENTION

The present invention relates generally to surgical lamps, and more particularly, to surgical lamps whose illuminance may be altered during use.

BACKGROUND OF THE INVENTION

In operating a modern surgical lamp, a light source in the surgical lamp is used to illuminate a work field, e.g., a surgical site. The area illuminated by the surgical lamp is typically called a light field. During a surgical procedure, a surgeon may adjust a pattern size of the light field for optimal viewing of the surgical site. As the pattern size of the light field is adjusted, it is beneficial to simultaneously adjust the light output of the surgical lamp. If the pattern size of the light field is reduced while the light output remains constant, the intensity of the light in the light field would increase. It is thus beneficial to simultaneously reduce the light output of the surgical lamp as the pattern size of the light field is reduced so that the intensity of the light in the light field remains substantially constant. In a similar fashion, as the pattern size of the light field is enlarged, it is beneficial to simultaneously increase the light output of the surgical lamp so that the intensity of the light in the light field remains substantially constant. In general, it is beneficial to maintain the intensity of the light in the light field substantially constant as the pattern size of the light field is changed during use.

The present invention provides a surgical lamp for controlling the light output of the surgical lamp both independently of, and simultaneously with, a change in a pattern size of the light field, to maintain a desired light intensity in the light field.

SUMMARY OF THE INVENTION

In accordance with the present invention, there is provided a method of controlling a light output of a surgical lamp. The surgical lamp is comprised of a housing that defines an internal cavity. A light source is disposed within the internal cavity of the housing, the light source producing a light path and a light field at a surgical site that is remote from the housing. The method comprises the steps of:

a) providing a voltage sensitive device along said light path, the voltage sensitive device having light transmissive properties that change in response to a biasing voltage applied thereto;

b) energizing the light source to create a light field at a surgical site; and c) applying a biasing voltage across the voltage sensitive device to change the light transmissive properties of the voltage sensitive device to achieve a desired light intensity at the surgical site.

An advantage of the present invention is a surgical lamp having a voltage sensitive device wherein a light transmissivity of the voltage sensitivity device changes in response to an applied voltage.

Another advantage of the present invention is a surgical lamp having a voltage sensitive device wherein an actual light intensity in a light field is maintained at a desired intensity of light regardless of a pattern size of the light field.

Another advantage of the present invention is a surgical lamp having a voltage sensitive device wherein an actual light intensity in a light field is maintained at a desired light intensity without physical contact, i.e., handling of the surgical lamp, by an operator to adjust a light output of the surgical lamp.

A further advantage of the present invention is a surgical lamp having a voltage sensitive device wherein the light transmissivity of the voltage sensitive device changes as a pattern size of a light field changes.

Yet another advantage of the present invention is a surgical lamp having a voltage sensitive device wherein the light transmissivity of the voltage sensitive device changes based on feedback from a sensor.

Yet another advantage of the present invention is a surgical lamp having a voltage sensitive device wherein the light transmissivity of the voltage sensitive device changes based on empirical data stored in a controller.

BRIEF DESCRIPTION OF THE DRAWINGS

The invention may take physical form in certain parts and arrangement of parts, a preferred embodiment of which will be described in detail in the specification and illustrated in the accompanying drawings, which form a part hereof, and wherein.

DETAILED DESCRIPTION OF A PREFERRED EMBODIMENT

Figure 1:
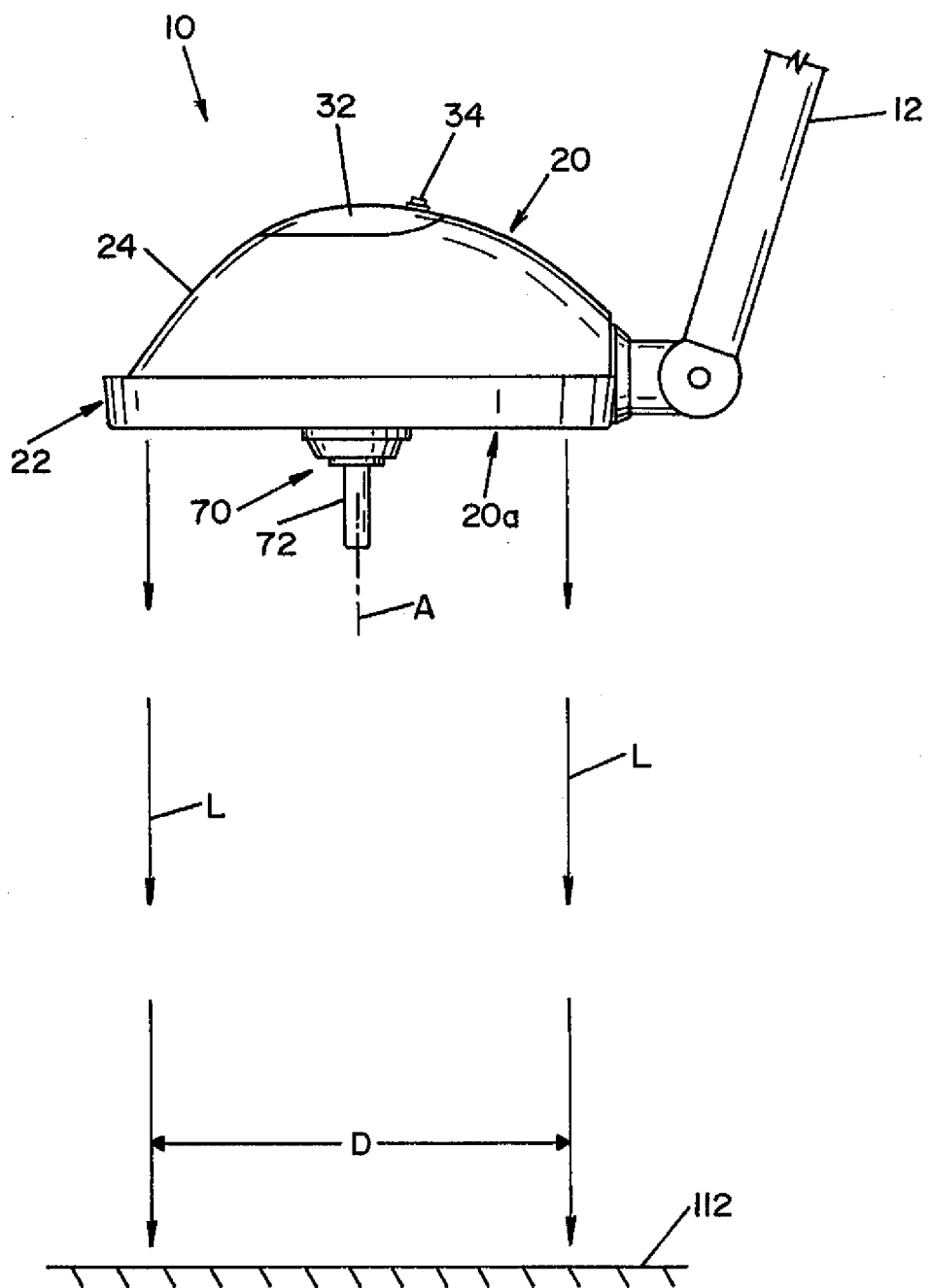
FIG. 1 is an elevational view of a surgical lamp in accordance with the present invention, showing a light field produced thereby, the light field having a diameter.

Referring now to the drawings wherein the showing is for the purpose of illustrating a preferred embodiment of the invention only and not for the purpose of limiting the same. FIG. 1 shows a surgical lamp 10 at an end of a support arm 12 that is partially shown. Surgical lamp 10 includes a housing 20.

Housing 20 is a domed-shaped element that has an open end 20a and defines an internal cavity 21. Housing 20 includes a mounting ring 22 and a cover 24, best seen in FIG. 2. Mounting ring 22 includes an inwardly projecting flange 26 disposed at a lower portion thereof. A mounting portion 28 of mounting ring 22 is dimensioned to attach to an end of support arm 12. In the embodiment shown, a portion of cover 24 is dimensioned to attach to the end of support arm 12. Cover 24 is attached to an upper portion of mounting ring 22. Cover 24 includes a lid 32 that is hinged to cover 24 to allow access to internal cavity 21. A locking mechanism 34 is provided to secure lid 32 in a closed position.

An insulator 36 is disposed on inwardly projecting flange 26 of mounting ring 22. Insulator 36 is a ring-shaped element. A recess 36a is formed in a bottom surface of insulator 36. An inwardly extending annular slot 36b is formed in an inner surface of insulator 36 above recess 36a. Insulator 36 is made of an insulating material that is resistant to the flow of electrical current therethrough. Insulator 36 is disposed on flange 26 of mounting ring 22 such that an annular slot is defined therebetween.

A protective lens 42 is dimensioned to be disposed across open end 20a of housing 20. Lens 42 is a disc-shaped element with an opening 42a in a center thereof. In the embodiment shown, opening 42a is circular in shape. An outer peripheral edge of lens 42 is dimensioned to be received into annular slot defined between flange 26 of mounting ring 22 and insulator 36. Lens 42 is made of a translucent material that allows light to pass therethrough.

Figure 2:
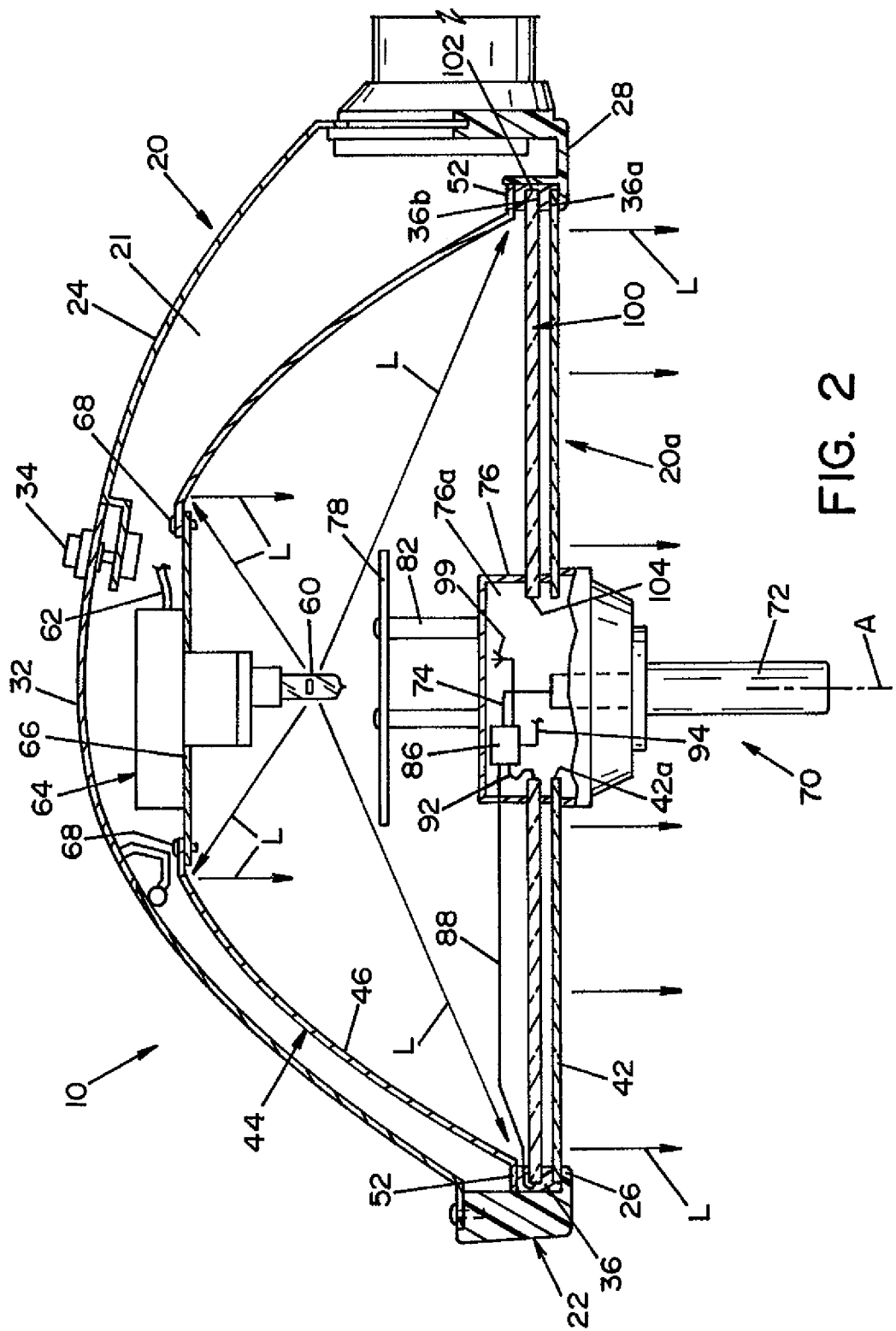
FIG. 2 is an enlarged, cross-sectional view of the surgical lamp shown in FIG. 1.
Figure 3:
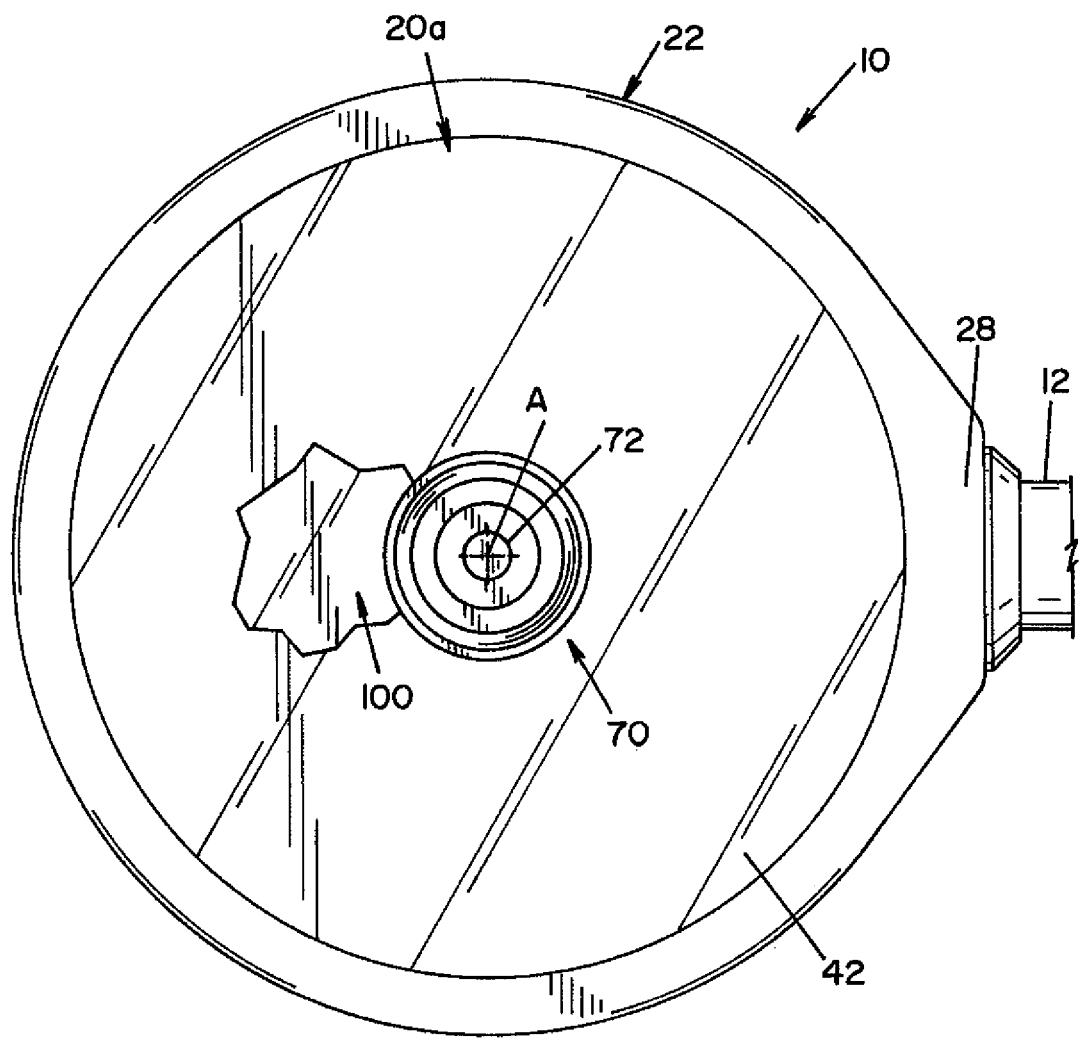
FIG. 3 is an enlarged, partially sectioned, bottom view of the surgical lamp shown in FIGS. 1 and 2.

A reflector 44 is dimensioned to be received into housing 20 above protective lens 42. Reflector 44 is a downward-facing, domed-shaped element with a curved inner surface 46. Reflector 44 is formed such that curved inner surface 46 of reflector 44 is highly reflective. An opening (not shown) is formed at a top of reflector 44. An outwardly extending flange 52 extends from a bottom of reflector 44. A bottom of flange 52 is dimensioned to be disposed on a top of insulator 36, as best seen in FIG. 2.

A housing 64 is disposed in the opening in the top of reflector 44. Housing 64 includes a mounting plate 66. A plurality of fasteners 68 secures mounting plate 66 to reflector 44. A light source 60 is attached to a lower portion of housing 64, as best seen in FIG. 2. Light source 60 is operable to emit light when supplied with electrical power. An electrical cable 62 extends from light source 60 to a source of power (not shown).

Surgical lamp 10 includes a light control assembly 70 to control a pattern size of a light field. Light control assembly 70 includes a housing 76 and a handle 72. Housing 76 is dimensioned to be received in opening 42a of lens 42. An upper portion of housing 76 is disposed above lens 42 and a lower portion of housing 76 is disposed below lens 42. Housing 76 defines an internal cavity 76a. A plate 78 is spaced above housing 76 by spacers 82. Bolts 84 attach plate 78 to spacers 82. Handle 72 is an elongated cylindrical element that is rotatably attached to the lower portion of housing 76 to be rotatable about an axis "A." Handle 72 is designed such that rotation of handle 72 causes the pattern size of the light field to increase or decrease. Handle 72 includes a feedback device (not shown) that is operable to provide signals indicative of the angular position or angular rotation of handle 72 about axis "A." The operation of handle 72 will be described in greater detail below.

A voltage sensitive device 100 is dimensioned to be received in open end 20a of housing 20, above lens 42. Voltage sensitive device 100 is a disc-shaped element with a circular opening 104 in a center thereof and an outer peripheral edge 102. Outer peripheral edge 102 of voltage sensitive device 100 is dimensioned to be received into slot 36b of insulator 36. Voltage sensitive device 100 is made of an electroactive, electrochromic material. As used herein, the term "electroactive, electrochromic material" means a material whose optical properties change when a voltage is applied thereto. More specifically, the light transmissivity of voltage sensitive device 100 changes when a biasing voltage is applied thereto. The light transmissivity of an object is a ratio of a total radiant or luminous flux transmitted by a transparent object to a luminous flux incident thereon. In this respect, the higher the transmissivity of an object, the more light that passes through the object.

Broadly stated, electrochromism is defined as a reversible optical change in a material induced by an external voltage. Many inorganic and organic materials show electrochromism. Some electrochromic materials change color/opacity with the application of a single voltage pulse. With these materials, once the color/opacity changes, no further voltage need be applied to the electrochromic material in order to maintain the new color/opacity of the electrochromic material. To change the color/opacity back to the original value or to change the color/opacity to a new value, one simply applies another, appropriate voltage pulse to the electrochromic material. With other electrochromic materials, a voltage must be applied and maintained across the electrochromic material for the electrochromic material to maintain its color/opacity.

By way of example and not limitation, electrochromic materials that are used to form electroactive, electrochromic voltage sensitive device 100 include: amorphous and crystalline metal oxides, transition-metal oxides, including, by way of example only, the high band-gap semiconductor tungsten oxide (WO3). Thin films of amorphous or polycrystalline WO3 are formed by various methods, including sol-gel methods, methods employing vacuum deposition, including, but not limited to, vacuum evaporation, vacuum sputtering and reactive vacuum sputtering. Other examples of inorganic materials that are used as electrochromic materials in the present invention include, but are not limited to, Prussian blue, oxides of: vanadium, niobium, molybdenum, titanium, cobalt and nickel.

It is also contemplated that organic materials are used to form voltage sensitive device 100. By way of example only, such organic materials include a bipyridilium or combinations of bipyridiliums or a conjugated polymer or combinations of conjugated polymers. Some of the electrochromic, conjugated polymers have rapid response times, i.e., under one second, making these materials advantageous for the present invention. In some instances, some of the conjugated electrochromic polymers have reaction times extending from about 900 milliseconds down to about 1 millisecond. Reaction times of some of the conjugated electrochromic polymers extend from about 50 milliseconds down to about 5 milliseconds, from about 20 milliseconds down to about 10 milliseconds and from about 18 milliseconds down to about 15 milliseconds. Examples of such conjugated polymers include, but are not limited to, derivatives of poly(thiophene), poly(pyrrole) and poly(aniline). Conjugated polymers may change from a transmissive and colorless state to a light gray. One such conjugated polymer that changes from a completely transmissive and colorless neutral state to a light gray oxidizing state upon an application of a voltage is poly(N-sulfonato-propoxy-3,4-propylenedioxypyrrole).

A work field 112 is disposed below surgical lamp 10. In the embodiment shown, work field 112 is a flat surface. It is also contemplated that work field 112 is a surgical site wherein a surgeon performs a surgical procedure in an operating room.

Figure 6:
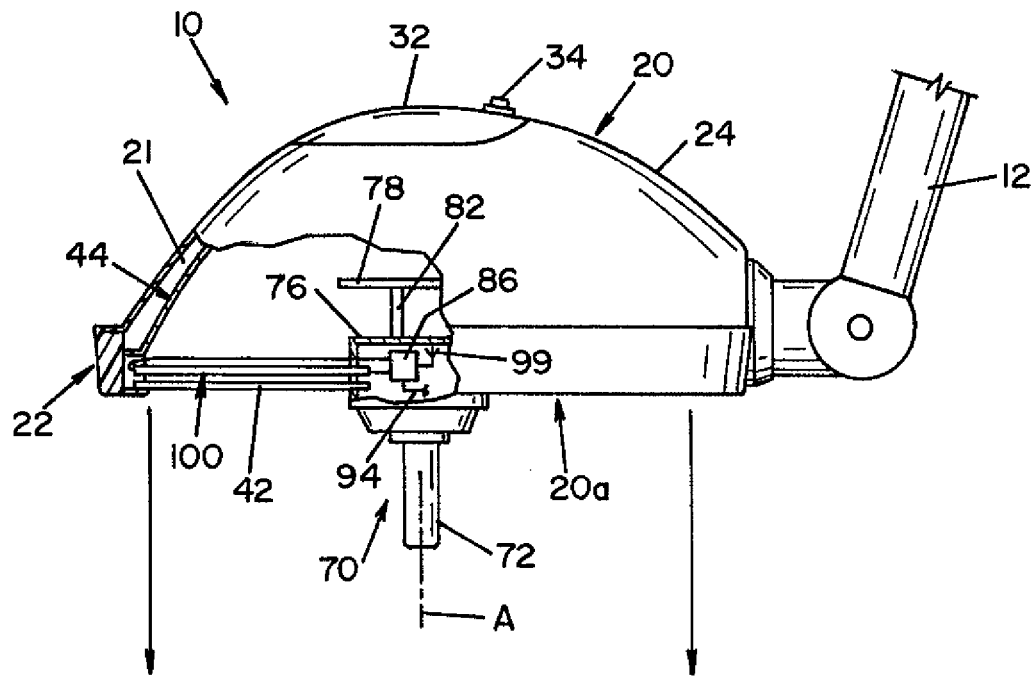
FIG. 6 is a partially sectioned, elevational view of a surgical lamp, illustrating a light intensity sensor on a work field.
Figure 6:
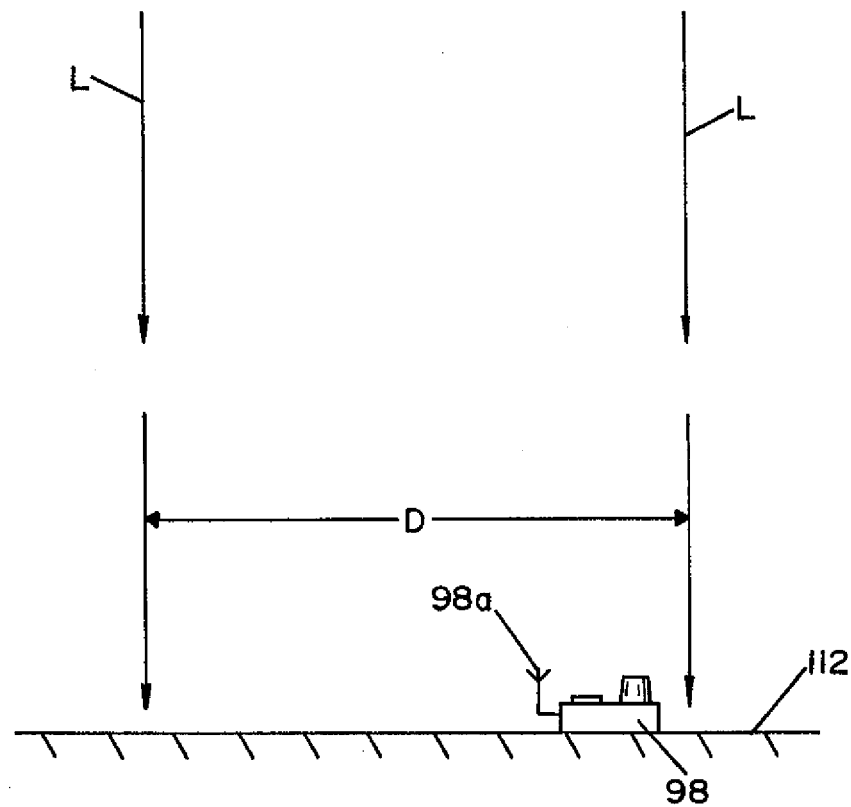

A portable light intensity sensor 98, best seen in FIG. 6, is disposed on work field 112. Portable light intensity sensor 98 is operable to detect the intensity of light on work field 112. A sending antenna 98a is attached to portable light intensity sensor 98. Portable light intensity sensor 98 is operable to provide electrical signals through sending antenna 98a to a receiver antenna 99 that is attached to a controller 86. The electrical signals are indicative of the intensity of light on work field 112.

Surgical lamp 10 includes a controller 86 to control a biasing voltage across voltage sensitive device 100. In the embodiment shown, controller 86 is dimensioned to be disposed in internal cavity 76a of housing 76. An electrical cable 94 extends from controller 86 to a power source (not shown). An electrical cable 74 extends from controller 86 to the feedback device in handle 72. In this respect, controller 86 is operable to receive signals from the feedback device in handle 72. The signals are indicative of the angular position or angular rotation of handle 72 about axis "A." A lead 88 connects one end of voltage sensitive device 100 to controller 86. A lead 92 connects another end of voltage sensitive device 100 to controller 86. Controller 86 is operable to provide a voltage difference across voltage sensitive device 100. As mentioned above, a receiving antenna 99 is attached to controller 86. In this respect, controller 86 is operable to receive signals through receiving antenna 99 from portable light intensity sensor 98. The signals are indicative of the intensity of light at work field 112. Broadly stated, controller 86 is programmed to control the biasing voltage applied across voltage sensitive device 100 to control the light transmissivity of voltage sensitive device 100 and thereby control the light output of surgical lamp 10.

The present invention shall now be described with respect to the operation of surgical lamp 10. Surgical lamp 10 is positioned above work field 112. As best seen in FIG. 6, light rays "L" propagate from surgical lamp 10 and are incident to work field 112 therebelow. The area illuminated by light rays "L" is typically called the "light field." In the embodiment shown, the light field is circular with a diameter "D." The light field may assume other configurations such as an oval or another non-circular profile. The size of the light field is typically called a "pattern size" of the light field. In some surgical lamps, the pattern size is changed by moving light source 60 relative to reflector 44. In this respect, handle 72 is used to control the pattern size of the light field by changing the position of light source 60 relative to reflector 44. Handle 72 is designed such that the rotation of handle 72 about axis "A," in a first direction, increases the pattern size of the light field. The rotation of handle 72 in a second direction, opposite the first direction, decreases the pattern size of the light field. In this respect, the surgeon is able to vary the pattern size of the light field during the surgical procedure.

"Light intensity" is a measure of the concentration of light per unit area. The light intensity of a light field is a function of the total light incident upon the light field and the pattern size of the light field. If the total light incident upon the light field is held constant and the pattern size of the light field is reduced, then the light intensity of the light field will increase. Similarly, if the pattern size of light field is held constant and the total light incident upon the light field is increased, the light intensity of the light field will increase. The intensity of the light field will decrease in a similar manner if one of the pattern size is increased or the total light output is decreased, while the other is held constant.

Due to the critical nature of surgical procedures, it is necessary that the light field provide optimal lighting conditions for the surgeon. A surgeon would typically set the intensity of the light in the light field at a "desired intensity" at the beginning of the surgical procedure. In addition, the surgeon would also set the pattern size of the light field at a "desired pattern size" at the beginning of the surgical procedure. Both the desired intensity and the desired pattern size are stored in a controller, such as controller 86 of the present invention.

A variety of other light sources, e.g., ambient lights, surgical lamps, computer monitors, etc., in the operating room contribute to this "desired intensity." During the course of the surgical procedure, the light output from one or more of the other light sources may change, thereby causing an "actual intensity" of light in the light field to deviate from the desired intensity. For example, when one or more of the other light sources is de-energized or energized, the total light incident on the light field may change. This, in turn, may change the intensity of the light in the light field. Similarly, when one or more of the other light sources moves or an object is disposed between the light source and the light field, the total light output incident on the light field may change. For example, during the surgical procedure, a nurse blocking light from one of the other light sources may reduce the total light incident on the light field. Furthermore, during the course of the surgical procedure, the surgeon may change the pattern size of the light field to aid in viewing the surgical site. This change in pattern size, without a change in light output, will cause the actual light intensity in the light field to change. The present invention provides a method and apparatus for controlling the light output of the surgical lamp both independently of, and simultaneously with, a change in a pattern size of the light field, to maintain a desired light intensity in the light field.

Figure 4:
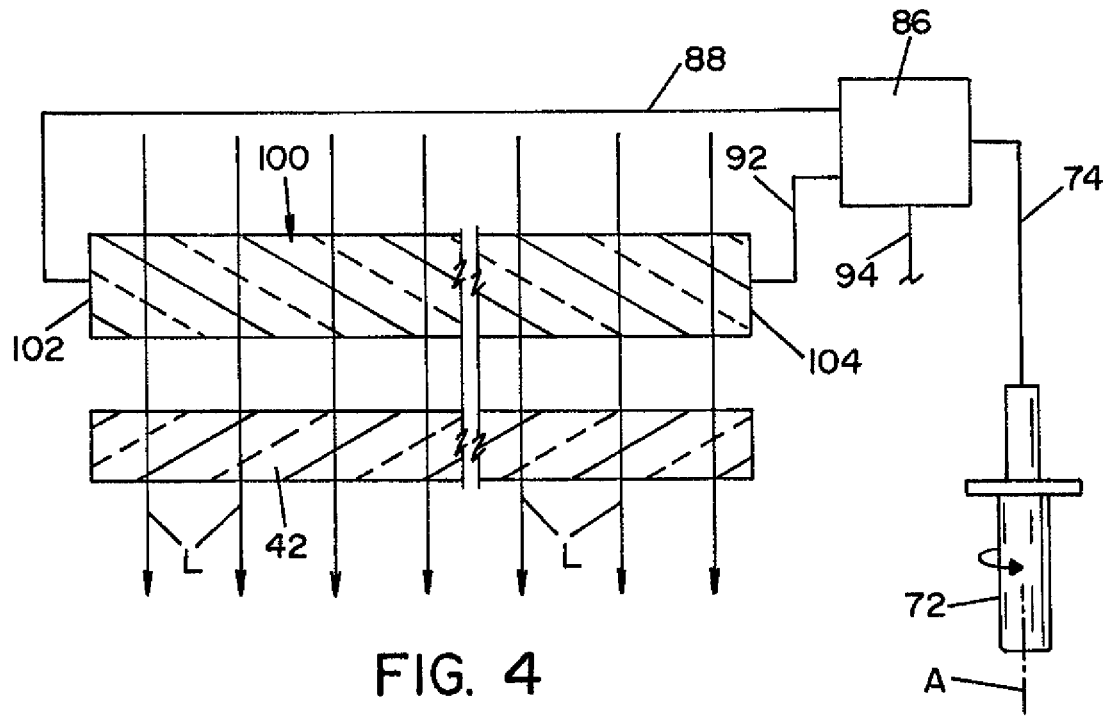
FIG. 4 is a schematic view of a voltage sensitive device illustrating a first condition wherein light passes therethrough.
Figure 5:
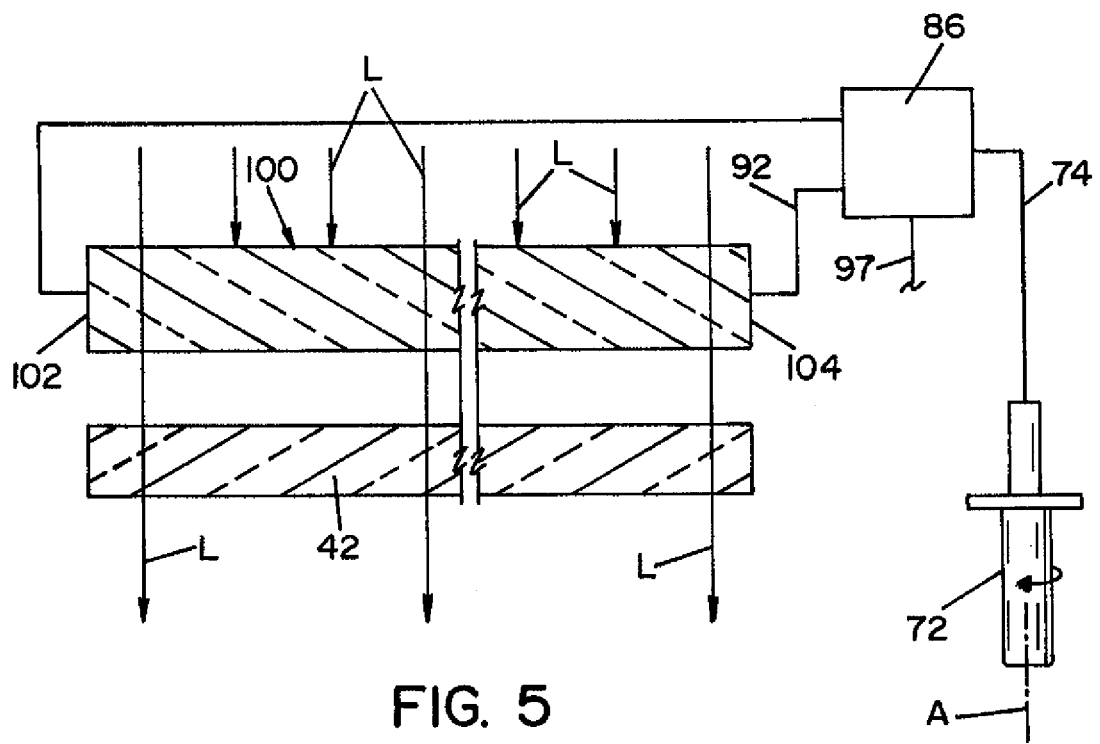
FIG. 5 is a schematic view of a voltage sensitive device illustrating a second condition wherein a portion of light incident on the voltage sensitive device passes therethrough.

During operation of the present invention, power is supplied to light source 60 by a power source (not shown). As illustrated in FIG. 2, light rays "L" from light source 60 are reflected by reflector 44 disposed within cover 24. Reflector 44 is dimensioned such that light rays "L" incident to reflector 44, are reflected, under the Law of Reflection, in a downward direction. Light rays "L" then propagate through voltage sensitive device 100 and protective layer 42 of surgical lamp 10, as best seen in FIGS. 4 and 5. The amount of light rays "L" that exit surgical lamp 10 depends on the light transmissivity of voltage sensitive device 100. FIG. 4 illustrates a first condition wherein a light transmissivity of voltage sensitive device 100 is set to allow a given amount of light rays "L" to pass through protective layer 42 and voltage sensitive device 100. FIG. 5 illustrates a second condition wherein the light transmissivity of voltage sensitive device 100 is reduced such that fewer light rays "L" pass through protective layer 42 and voltage sensitive device 100.

The present invention is designed to simultaneously operate in a first mode and a second mode. In the first mode, the present invention maintains a desired light intensity in the light field, regardless of changes to the pattern size of the light field. In the second mode, the present invention maintains the desired light intensity in the light field, based on changes to the pattern size of the light field.

In accordance with the first mode, controller 86 is programmed to maintain a desired light intensity in a light field, regardless of changes to the pattern size of the light field. As stated above, at the beginning of a surgical procedure, a surgeon sets the intensity of the light in the light field at the "desired intensity." Portable light intensity sensor 98 provides signals to controller 86 indicative of the intensity of light in the light field. Controller 86 then stores the desired intensity. Controller 86 is programmed such that, during the surgical procedure, controller 86 receives signals from portable light intensity sensor 98 that are indicative of the light intensity in the light field. Controller 86 is programmed to apply a biasing voltage across voltage sensitive device 100 to maintain a desired light intensity in the light field. For example, controller 86 is programmed such that if the actual light intensity in the light field, as measured by portable light intensity sensor 98, is lower than the desired light intensity, controller 86 will apply a biasing voltage across voltage sensitive device 100 to increase the transmissivity of voltage sensitive device 100. The increase in transmissivity of voltage sensitive device 100 increases the light output of surgical lamp 10, thereby increasing the actual light intensity in the light field. Controller 86 is also programmed such that if the actual light intensity in the light field is higher than the desired intensity, controller 86 will apply a biasing voltage to voltage sensitive device 100 to decrease the transmissivity of voltage sensitive device 100. The decrease in transmissivity of voltage sensitive device 100 decreases the light output of surgical lamp 10, thereby decreasing the actual light intensity in the light field.

It is contemplated that for the first mode, the biasing voltage applied to voltage sensitive device 100 is determined based on one of three different control methods. In the first control method, controller 86 is programmed to determine a difference between the actual light intensity in a light field and the desired light intensity and apply a biasing voltage across voltage sensitive device 100 based on the difference. In the second control method, controller 86 is programmed to incrementally adjust the biasing voltage to voltage sensitive device 100 until the actual light intensity in the light field equals the desired light intensity. In a third control method, controller 86 is programmed to calculate a difference between the actual light intensity and the desired light intensity, and based on a "look-up table" stored in controller 86, apply a biasing voltage to voltage sensitive device 100. In this respect, the present invention provides a method and apparatus for controlling a light output of a surgical lamp to maintain a desired light intensity level in a light field, dependent on factors other than changes to the pattern size of the light field.

In accordance with the second mode of the present invention, controller 86 is programmed to maintain a desired light intensity in a light field, based on changes to the pattern size of the light field. As described above, in addition to setting the light intensity in the light field at a "desired light intensity," at the beginning of the surgical procedure, the surgeon also sets the pattern size of the light field at a "desired pattern size." Portable light intensity sensor 98 provides a signal to controller 86 indicative of the desired light intensity of the light field. The feedback device in handle 72 provides a signal to controller 86 indicative of the desired pattern size of the light field. Controller 86 stores both the desired light intensity and the desired pattern size.

During the course of the surgical procedure, the surgeon may change the pattern size of the light field from the desired pattern size, by rotation of handle 72 about axis "A." Handle 72 sends electrical signals to controller 86 that are indicative of a change in pattern size of the light field. Based on the electrical signals, controller 86 applies a biasing voltage across voltage sensitive device 100 to change the light transmissivity of voltage sensitive device 100. The change in light transmissivity of voltage sensitive device 100 changes the light output of surgical lamp 10 to maintain the light intensity in the light field at the desired light intensity level. For example, if the surgeon reduces the pattern size of the light field by rotating handle 72 of surgical lamp 10, electrical signals that correspond to the rotation of handle 72 are sent to controller 86 by handle 72. Based on the electrical signals from handle 72, controller 86 applies a biasing voltage across voltage sensitive device 100 to lower the transmissivity of voltage sensitive device 100, thereby reducing the light output of surgical lamp 10 and maintaining the intensity of the light in the light field. Similarly, when the pattern size of the light field is increased, controller 86 is programmed to increase the transmissivity of voltage sensitive device 100. As a result, the light output of surgical lamp 10 is increased to maintain the intensity of the light in the light field at the desired light intensity level.

It is contemplated that for the second mode of operation, the biasing voltage applied to voltage sensitive device 100 is determined based on one of two control methods. In the first control method, controller 86 is programmed to calculate a difference between the value of the electrical signal for the desired pattern size and the value of the electrical signal for the new pattern size and apply a biasing voltage based on the difference. In the second control method, controller 86 is pre-programmed such that as handle 72 is rotated, controller 86 simultaneously applies a biasing voltage to voltage sensitive device 100 based on the change in the rotational position of handle 72. For example, it is contemplated that in another embodiment of the present invention (not shown), a voltage control device, such as a rheostat, is attached to handle 72. Leads connect the voltage control device to controller 86 and to the power source. The voltage control device is designed such that the rotation of handle 72 causes a change in an electrical resistance of the voltage control device. The electrical resistance of the voltage control device determines the voltage that is supplied to controller 86 and, in turn, the biasing voltage applied across voltage sensitive device 100. In this respect, the rotation of handle 72 simultaneously changes the pattern size of the light field and the biasing voltage applied to voltage sensitive device 100. Regardless of the control method, the present invention provides a method and apparatus that changes a light output of a surgical lamp based on a pattern size of a light field.

It is also contemplated that voltage sensitive device 100 is comprised of a plurality of elements or panels to achieve a desired variation of light intensity in the light field. It is believed that, for some surgical procedures, a surgeon needs a higher intensity of light in the center of the light field and a lower intensity of light near the outer edges of the light field. To achieve the desired variation in light intensity, a circular center region of voltage sensitive device 100 is one element or panel while an annular ring around the center region is another element or panel. In this respect, the light intensity in the center of the light field and the light intensity near the edge of the light field can be set at two different light intensity levels. It is also contemplated that voltage sensitive device 100 is comprised of more than two (2) elements or panels such that the light intensity in two (2) or more regions of the light field can be set at different intensity levels. In one embodiment (not shown), each element or panel is comprised of the same electrochromic material. In another embodiment (not shown), each element or panel is comprised of a different electrochromic material. It is also contemplated that the present invention includes a plurality of portable light intensity sensors 98. Each of the plurality of light sensors 98 provides electrical signals indicative of the light intensity in a discrete region of the light field. Controller 86 is programmed, as described above, to maintain a desired light intensity in each of the discrete regions of the light field.

Figure 7:
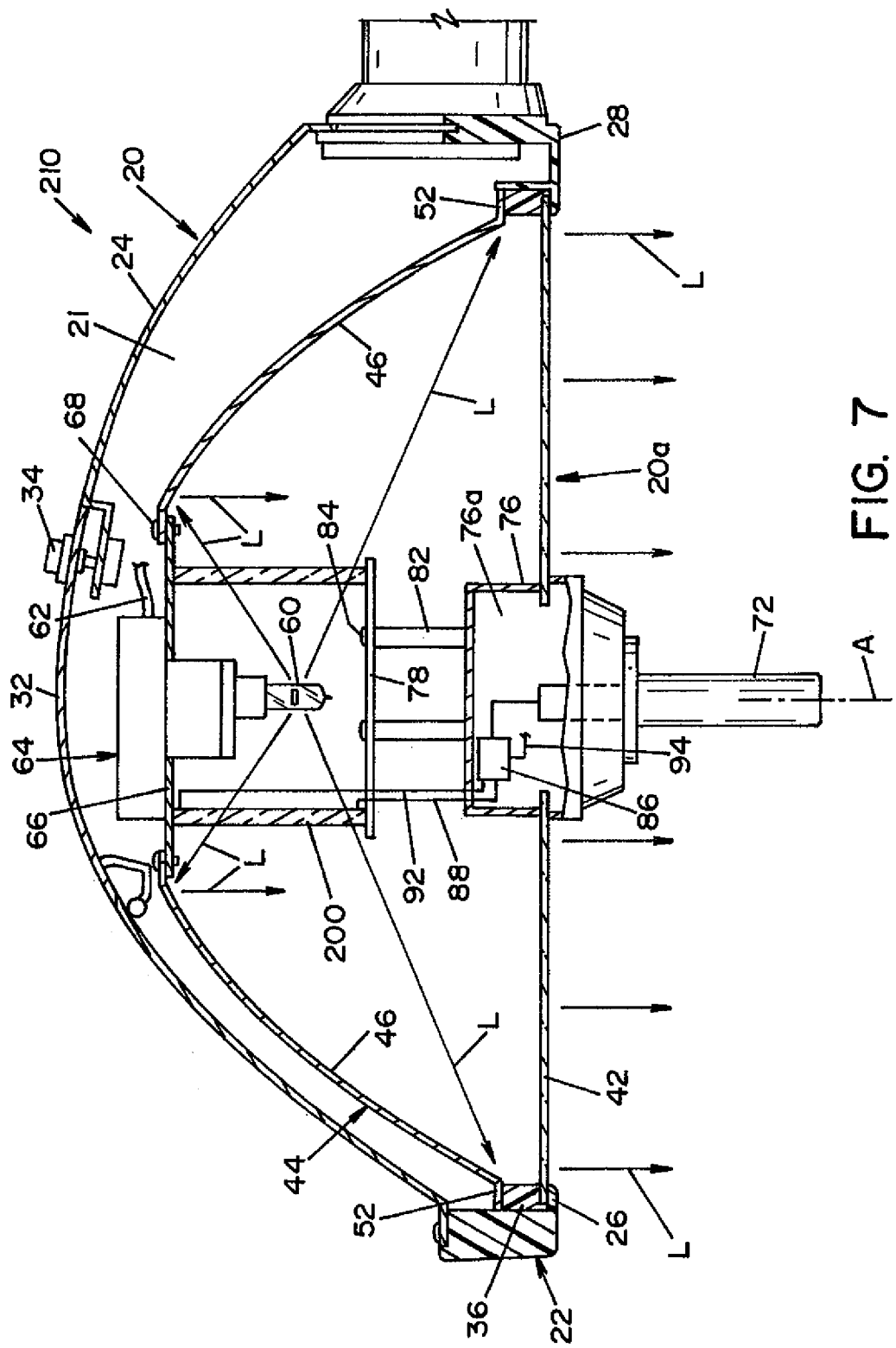
FIG. 7 is an enlarged, cross-sectional view of a surgical lamp showing an alternative embodiment of the present invention.

Referring now to FIG. 7, a surgical lamp 210 illustrating another embodiment of the present invention is shown. Parts that are similar to the first embodiment of the present invention have been given similar numbers. Voltage sensitive device 200 is a cylindrical element that is attached to mounting plate 66 and extends downward toward plate 78. In this respect, voltage sensitive device 200 is disposed between light source 60 and reflector 44. The light transmissivity of the voltage sensitive device 200 is controlled, as described above, to maintain a light intensity in a light field at a desired light intensity level.

Other modifications and alterations will occur to others upon their reading and understanding of the specification. It is intended that all such modifications and alterations be included insofar as they come within the scope of the invention as claimed or the equivalents thereof.

Having described the invention, the following is claimed:

1. A method of controlling a light output of a surgical lamp using a voltage sensitive device having light transmissive properties that change in response to a biasing voltage applied thereto, said surgical lamp comprised of a housing defining an internal cavity and a light source disposed within said internal cavity of said housing, said light source producing a light path and a light field at a surgical site that is remote from said housing, said method comprising the steps of:
 providing a voltage sensitive device along said light path, said voltage sensitive device having light transmissive properties that change in response to changes in a biasing voltage applied thereto;
 energizing said light source to create a light path to said surgical site and a light field at a surgical site, said light source creating an actual light intensity at said surgical site;
 comparing said actual light intensity at said surgical site to a desired light intensity; and
 modifying said biasing voltage across said voltage sensitive device to change said light transmissive properties of said voltage sensitive device until said actual light intensity at said surgical site is equal to said desired light intensity.

2. A method as defined in claim 1, wherein said surgical lamp includes a handle operable to adjust a pattern size of said light field, and said method further comprises the steps of:
 adjusting said biasing voltage across said voltage sensitive device when said handle is operated to adjust said pattern size of said light field.

3. A method as defined in claim 2, wherein said step of adjusting said biasing voltage includes controlling said biasing voltage to said voltage sensitive device such that a light intensity at said surgical site remains constant as said pattern size of said light field changes.

4. A method as defined in claim 3, wherein said surgical lamp includes a voltage control device attached to said handle, and said method further comprises:
 operating said voltage control device to control said biasing voltage to said voltage sensitive device based on a rotational position of said handle.

5. A method as defined in claim 3, wherein said surgical lamp includes control means comprised of:
 a feedback device disposed on said handle, said feedback device operable to provide a signal indicative of a rotational position of said handle; and
 a controller operable to receive said signal from said feedback device and control said biasing voltage to said voltage sensitive device based on said signal from said feedback device.

6. A method as defined in claim 1, wherein said step of adjusting includes determining an actual light intensity at said surgical site.

* * * * *